(12) United States Patent
Lizardi et al.

(10) Patent No.: US 10,045,771 B2
(45) Date of Patent: Aug. 14, 2018

(54) KNOTLESS SUTURE ANCHOR

(71) Applicant: DePuy Mitek, LLC, Raynham, MA (US)

(72) Inventors: Jose E. Lizardi, Raynham, MA (US); Meghan Vento, Raynham, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 467 days.

(21) Appl. No.: 13/959,770

(22) Filed: Aug. 6, 2013

(65) Prior Publication Data

US 2013/0325064 A1 Dec. 5, 2013

Related U.S. Application Data

(62) Division of application No. 13/247,132, filed on Sep. 28, 2011, now Pat. No. 8,535,350.

(51) Int. Cl.
*A61B 17/04* (2006.01)
(52) U.S. Cl.
CPC .... *A61B 17/0401* (2013.01); *A61B 2017/044* (2013.01); *A61B 2017/0409* (2013.01); *A61B 2017/0433* (2013.01); *A61B 2017/0438* (2013.01); *A61B 2017/0448* (2013.01); *A61B 2017/0451* (2013.01); *A61B 2017/0453* (2013.01)
(58) Field of Classification Search
CPC . A61B 2017/0403–2017/0464; A61B 17/0401
See application file for complete search history.

(56) References Cited

U.S. PATENT DOCUMENTS

| 4,105,034 A | 8/1978 | Shalaby et al. |
| 4,130,639 A | 12/1978 | Shalaby et al. |
| 4,140,678 A | 2/1979 | Shalaby et al. |

(Continued)

FOREIGN PATENT DOCUMENTS

| CN | 101094618 A | 12/2007 |
| CN | 101237829 A | 8/2008 |

(Continued)

OTHER PUBLICATIONS

Kemnitzer and Kohn, Handbook of Biodegradable Polymers, edited by Domb, et. al., Hardwood Academic Press, 1997, pp. 251-272.

(Continued)

*Primary Examiner* — Shaun L David

(57) ABSTRACT

A suture anchor comprises a shell and an anchor member. The shell comprises a body having a distal end, a proximal end and sidewalls therebetween defining an axial cannulation therethrough. The anchor member comprises a body having a distal end and a proximal end which is sized to fit within the cannulation. The sidewalls define a lateral cut-out such that with the anchor member received within the cannulation a first lateral portion of the anchor member is exposed laterally and a second, laterally opposite, lateral portion of the anchor member is enclosed by the sidewalls. A friction enhancement on the first lateral portion frictionally engages a bone surface when the suture anchor is disposed within a bone tunnel defined by the bone surface. Suture is trapped between the shell and the anchor and also between the anchor and the bone surface.

10 Claims, 8 Drawing Sheets

(56) References Cited

U.S. PATENT DOCUMENTS

| | | | |
|---|---|---|---|
| 4,141,087 A | 2/1979 | Shalaby et al. | |
| 4,205,399 A | 6/1980 | Shalaby et al. | |
| 4,208,511 A | 6/1980 | Shalaby et al. | |
| 5,324,308 A * | 6/1994 | Pierce | A61B 17/0401 606/232 |
| 5,464,929 A | 11/1995 | Bezwada et al. | |
| 5,595,751 A | 1/1997 | Bezwada et al. | |
| 5,597,579 A | 1/1997 | Bezwada et al. | |
| 5,607,687 A | 3/1997 | Bezwada et al. | |
| 5,618,552 A | 4/1997 | Bezwada et al. | |
| 5,620,698 A | 4/1997 | Bezwada et al. | |
| 5,632,748 A * | 5/1997 | Beck, Jr. | A61F 2/0811 606/232 |
| 5,645,850 A | 7/1997 | Bezwada et al. | |
| 5,648,088 A | 7/1997 | Bezwada et al. | |
| 5,698,213 A | 12/1997 | Jamiolkowski et al. | |
| 5,700,583 A | 12/1997 | Jamiolkowski et al. | |
| 5,859,150 A | 1/1999 | Jamiolkowski et al. | |
| 5,935,129 A * | 8/1999 | McDevitt | A61B 17/0401 606/232 |
| 6,162,234 A * | 12/2000 | Freedland | A61B 17/0401 411/344 |
| 7,081,126 B2 | 7/2006 | McDevitt et al. | |
| 7,648,524 B2 | 1/2010 | Zhang et al. | |
| 8,029,537 B2 | 10/2011 | West, Jr. et al. | |
| 8,613,756 B2 | 12/2013 | Lizardi et al. | |
| 9,125,696 B2 | 9/2015 | Linke | |
| 2003/0187444 A1* | 10/2003 | Overaker | A61B 17/0401 606/232 |
| 2006/0052787 A1 | 3/2006 | Re et al. | |
| 2008/0027430 A1 | 1/2008 | Montgomery et al. | |
| 2008/0161864 A1 | 7/2008 | Beck et al. | |
| 2008/0275469 A1 | 11/2008 | Fanton et al. | |
| 2009/0312794 A1 | 12/2009 | Nason et al. | |
| 2010/0262185 A1 | 10/2010 | Gelfand et al. | |
| 2010/0292732 A1 | 11/2010 | Hirotsuka et al. | |
| 2010/0292733 A1 | 11/2010 | Hendricksen et al. | |
| 2013/0006278 A1* | 1/2013 | Mayer | A61B 17/686 606/151 |

FOREIGN PATENT DOCUMENTS

| | | | | |
|---|---|---|---|---|
| CN | 102113901 A | | 7/2011 | |
| JP | 2003-528648 | | 9/2003 | |
| JP | 2005-504555 | | 2/2005 | |
| WO | WO 95/11631 A1 | | 5/1995 | |
| WO | WO 2011091545 A1 * | | 8/2011 | A61B 17/686 |

OTHER PUBLICATIONS

Cohn and Younes, Journal of Biomaterials Research, 1998, pp. 993-1009, vol. 22.

Cohn, Polymer Preprints (ACS Division of Polymer Chemistry), 1989, p. 498, vol. 30(1).

Allcock, Encyclopedia of Polymer Science, Wiley Intersciences, John Wiley & Sons, 1988, pp. 31-41, vol. 13.

Vandorpe, et al., Handbook of Biodegradable Polymers, edited by Domb, et al., Hardwood Academic Press, 1997, pp. 161-182.

Handbook of Biodegradable Polymers, edited by Domb, et al., Hardwood Academic Press, 1997, pp. 99-118.

* cited by examiner

KNOTLESS SUTURE ANCHOR

CROSS REFERENCE TO RELATED APPLICATIONS

This application is a divisional application of U.S. patent application Ser. No. 13/247,132, entitled KNOTLESS SUTURE ANCHOR, filed Sep. 28, 2011, which is incorporated herein by reference.

BACKGROUND

This application relates to suture anchors and more particularly to knotless suture anchors.

Knotless suture anchors allow fixation of suture to bone without requiring a surgeon to tie a knot to fix the suture with respect to the anchor. Certain knotless anchors capture suture in a notch at their distal end and are then inserted into a bone tunnel trapping the suture between the anchor and the bone to effect fixation. In soft bone the suture may cut into the bone over time, thereby loosening the tension in the suture. Certain other designs capture the suture between interlocking parts which also expand outwardly to limit their retraction from a bone tunnel. These anchors have many benefits but do not typically achieve the same level of fixation into bone as a regular threaded anchor.

SUMMARY OF THE INVENTION

The present invention overcomes these and other limitations of the prior art in a simple and elegant design.

A suture anchor according to the present invention comprises a shell and an anchor member. The shell comprises a body having a distal end, a proximal end and sidewalls therebetween defining an axial cannulation therethrough. The anchor member comprises a body having a distal end and a proximal end sized to fit within the cannulation. The sidewalls define a lateral cut-out such that with the anchor member received within the cannulation a first lateral portion of the anchor member is exposed laterally and a second, laterally opposite, lateral portion of the anchor member is enclosed by the sidewalls. A friction enhancement on the first lateral portion is adapted to frictionally engage a bone surface when the suture anchor is disposed within a bone tunnel defined by the bone surface.

Preferably, the friction enhancement comprises exterior threading about the anchor member body. Also preferably, complimentary internal threading is provided on an interior surface of the sidewall engaged with the exterior threading of the anchor member body.

Preferably, the cut-out extends to the shell proximal end. Preferably, the shell distal end completely encircles the anchor member.

Preferably, a distal portion of the anchor member is smooth and free of the friction enhancement, thus easing its entry and alignment into the bone tunnel.

Preferably, one or more sutures are locked between the sidewall and the anchor member. An axially extending suture receiving recess can be provided along the sidewall adjacent the anchor member second lateral portion configured to keep the suture positioned therein despite rotation of the anchor member relative to the shell. Preferably, the suture extends proximally out of the shell over its proximal end so that the shell can act to protect the bone forming the bone tunnel from being abraded by the suture.

In one aspect of the invention, a suture is threaded distally down the cannulation between the sidewall and the anchor member, out of the cannulation at the shell distal end and up along the anchor member first lateral portion.

In another aspect of the invention, a suture threader extends between the anchor member and the sidewalls. The threader comprises an elongated flexible member which extends out of the shell proximal end and terminates in a suture capture configuration. Preferably, the suture capture configuration comprises a suture capture loop.

A method according to the present invention provides for anchoring a soft tissue to a bone. The method comprises the steps of: threading a suture through the soft tissue; preparing a bone tunnel in the bone; positioning a shell of a suture anchor into the bone tunnel, and engaging an anchor member with the shell. The shell comprises a body having a distal end, a proximal end and sidewalls therebetween defining an axial cannulation therethrough. The anchor member is disposed within the cannulation with the suture extending from the soft tissue between the anchor member and the sidewall and the step of engaging locks the suture between the anchor member and the sidewall.

Preferably, prior to engaging the anchor member with the shell, the suture extending from the soft tissue is tensioned to a desired extent.

Preferably, the suture is also locked between the anchor member and the bone in the bone tunnel.

Preferably, the suture extends out of the bone hole by extending out of the shell over its proximal end toward the tissue whereby the shell thus reduces chafing between the suture and the bone.

DETAILED DESCRIPTION

Figure 1:
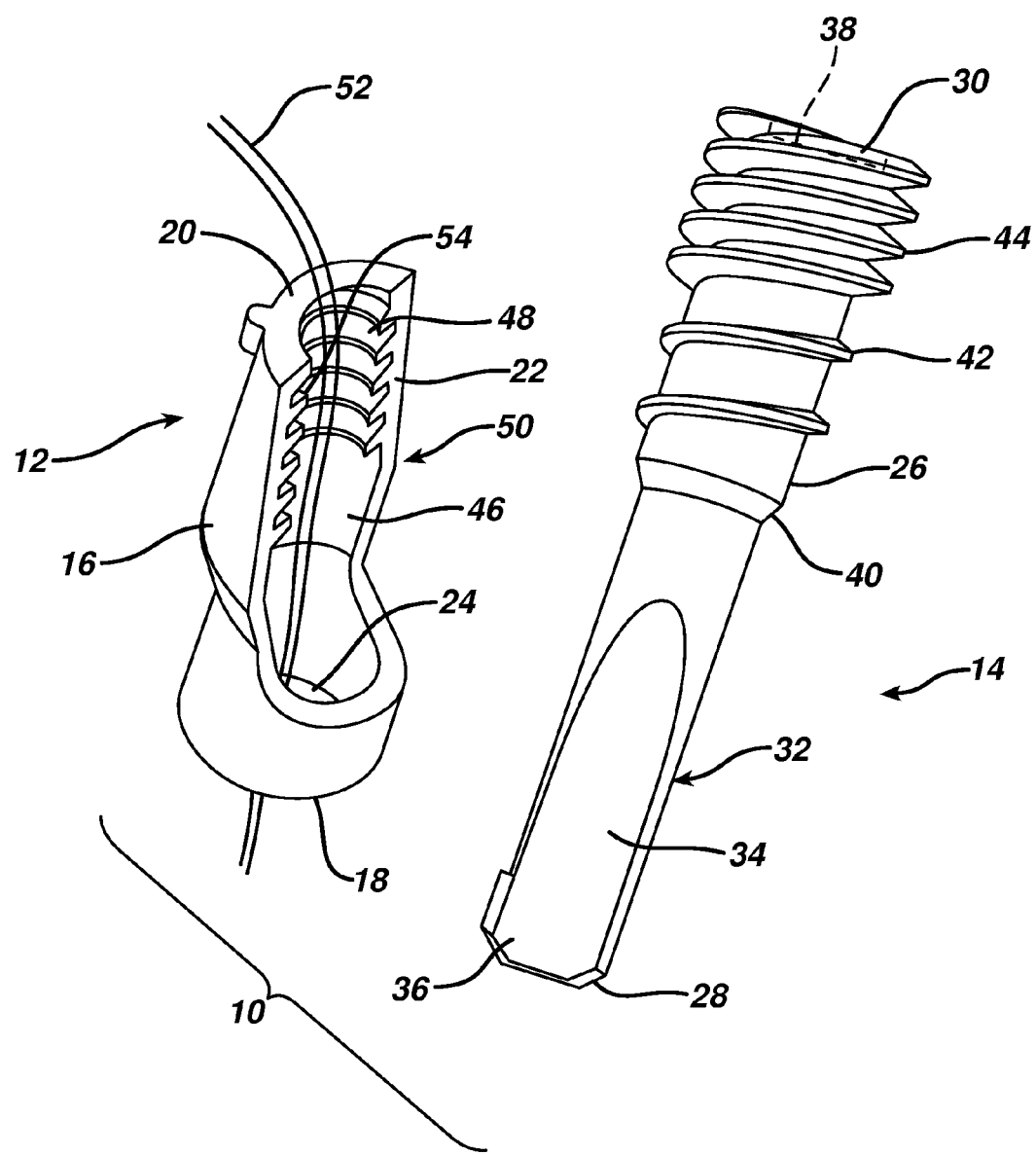
FIG. 1 is an exploded perspective view of a suture anchor according to the present invention.

FIG. 1 illustrates a suture anchor 10 according to the present invention. It comprises a shell 12 and an anchor member 14 for receipt within the shell 12. The shell 12 comprises a body 16 having a distal end 18 and a proximal end 20 with sidewalls 22 therebetween defining an axial cannulation 24 adapted to receive the anchor member 14.

The anchor member 14 comprises an elongated body 26 having a distal end 28 and a proximal end 30 and which is sized to fit within the cannulation 24. A distal nose 32 of the body 26 has a reduced diameter and a smooth outer surface 34 lacking threading. A chamfer 36 at the distal end 28 eases entry into a bone tunnel (not shown in FIG. 1). A tool engaging recess 38, for example a hexagonal shape, is provided at the body proximal end 30. The body proximal end 30 has a slightly larger diameter creating a boss 40 at the smaller distal nose 32. Bone engaging threads 42 encircle the body 26 at its proximal end 30 and extend to the boss 40, with a second start of parallel threads 44 at the proximal end 30 for additional holding in harder cortical bone (not shown in FIG. 1).

The sidewalls 22 at the shell distal end 18 encircle the cannulation 24 and have an internal diameter sized to accommodate the anchor member distal nose 32. The sidewalls 22 at the shell proximal end 20 have a larger internal diameter sized to accommodate the anchor member body proximal end 30, thus creating a boss 46 which engages the boss 40 to limit distal movement of the anchor member 14 through the shell 12. Internal threads 48 on the sidewalls 22 at the proximal end 20 mate with the threads 42 and 44. The sidewalls 22 do not enclose the cannulation 24 at the proximal end 20 but rather open to form a lateral cut-out 50 exposing one side of the anchor member 14 including the threads 42 and 44.

The shell 12 is adapted to receive one or more sutures 52 through the cannulation 24 and between the shell 12 and anchor member 14. A longitudinal suture path 54 is created by a reduction in the crest height of the internal threads 48 therealong. Suture 52 in the path tends to thus not be moved out of the path 54 by the interaction of the threads 42 and 44 with the threads 48.

The crest height, or diameter, of the threads 42 and 44 is larger at the proximal end 30 of the anchor member 14. A smaller diameter on the distal threads 42 allows a "smaller profile" of the device construct as it enters a bone hole (not shown if FIG. 1). After the shell 12 is advanced into the bone hole, the anchor member 14 is rotated and driven relative to the static shell 12. The larger proximal threads 42 and 44 force the shell 12 to expand and also compress the suture strands 52 between the two components.

The suture anchor 10 is formed of a suitable biocompatible material and is preferably provided sterile and packaged within a bacteria-proof enclosure (not shown) such that it is ready for a sterile surgical procedure. Many biodegradable materials have less strength and are more brittle than non-biodegradable materials such as PEEK polymer (polyetheretherketone) or stainless steel. The simple design of the anchor 10, allows easier use of such biodegradable materials while maintaining structural integrity.

The novel suture anchors of the present invention may be made from a metallic material, a non-biodegradable polymer, a biodegradable polymer, or a composite of a biodegradable polymer or copolymer and a bioceramic. The term biodegradable as used herein is defined to mean materials that degrade in the body and then are either absorbed into or excreted from the body. The term bioceramic as defined herein is defined to mean ceramic and glass materials that are compatible with body tissue. The bioceramics are preferably biodegradable.

The metallic materials that can be used to manufacture the anchors of the present invention include stainless steel, titanium, alloys of nickel and titanium, or other biocompatible metallic materials.

The non-biodegradable materials that can be used to manufacture the anchors of the present invention include polyethylene, polypropylene, PEEK, or other biocompatible non-absorbable polymers.

The biodegradable polymers that can be used to manufacture the anchors used in the present invention include biodegradable polymers selected from the group consisting of aliphatic polyesters, polyorthoesters, polyanhydrides, polycarbonates, polyurethanes, polyamides and polyalkylene oxides. Preferably, the biodegradable polymers are aliphatic polyester polymers and copolymers, and blends thereof. The aliphatic polyesters are typically synthesized in a ring opening polymerization. Suitable monomers include but are not limited to lactic acid, lactide (including L-, D-, meso and D,L mixtures), glycolic acid, glycolide, .epsilon.-caprolactone, p-dioxanone (1,4-dioxan-2-one), trimethylene carbonate (1,3-dioxan-2-one), .delta.-valerolactone, and combinations thereof.

The bioceramics that can be used in the composite anchors of the present invention include ceramics comprising mono-, di-, tri-, .alpha.-tri-, .beta.-tri-, and tetra-calcium phosphate, hydroxyapatite, calcium sulfates, calcium oxides, calcium carbonates, magnesium calcium phosphates. It is particularly preferred to use a .beta.-tritricalcium phosphate. In addition to bioceramics, bioglasses may also be used in the composite screws. The bioglasses may include phosphate glasses and bioglasses.

Suitable biocompatible synthetic polymers can include polymers selected from the group consisting of aliphatic polyesters, poly(amino acids), copoly(ether-esters), polyalkylene oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, polyurethanes, poly (ether urethanes), poly(ester urethanes), polypropylene fumarate), poly(hydroxyalkanoate) and blends thereof.

For the purpose of this invention aliphatic polyesters include, but are not limited to, homopolymers and copolymers of lactide (which includes lactic acid, D-,L- and meso lactide); glycolide (including glycolic acid); .epsilon.-caprolactone; p-dioxanone (1,4-dioxan-2-one); trimethylene carbonate (1,3-dioxan-2-one); alkyl derivatives of trimethylene carbonate; .delta.-valerolactone; .beta.-butyrolactone; .gamma.-butyrolactone; .epsilon.-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; .alpha.,.alpha. diethylpropiolactone; ethylene carbonate; ethylene oxalate; 3-methyl-1, 4-dioxane-2,5-dione; 3,3-diethyl-1,4-dioxan-2,5-dione-; 6,6-dimethyl-dioxepan-2-one; 6,8-dioxabicycloctane-7-one and polymer blends thereof. Additional exemplary polymer or polymer blends include, by non-limiting example, a polydioxanone, a polyhydroxybutyrate-co-hydrox-yvalerate, polyorthocarbonate, a polyaminocarbonate, and a polytrimethylene carbonate. Aliphatic polyesters used in the present invention can be homopolymers or copolymers (random, block, segmented, tapered blocks, graft, triblock, etc.) having a linear, branched or star structure. Poly(iminocarbonates), for the purpose of this invention, are understood to include those polymers as described by Kemnitzer and Kohn, in the Handbook of Biodegradable Polymers, edited by Domb, et. al., Hardwood Academic Press, pp. 251-272 (1997). Copoly(ether-esters), for the purpose of this invention, are understood to include those copolyester-ethers as described in the Journal of Biomaterials Research, Vol. 22, pages 993-1009, 1988 by Cohn and Younes, and in Polymer Preprints (ACS Division of Polymer Chemistry), Vol. 30(1), page 498, 1989 by Cohn (e.g., PEO/PLA). Polyalkylene oxalates, for the purpose of this invention, include those described in U.S. Pat. Nos. 4,208,511; 4,141, 087; 4,130,639; 4,140,678; 4,105,034; and 4,205,399. Polyphosphazenes, co-, ter- and higher order mixed monomer based polymers made from L-lactide, D,L-lactide, lactic acid, glycolide, glycolic acid, para-dioxanone, trimethylene carbonate and E-caprolactone such as are described by Allcock in The Encyclopedia of Polymer Science, Vol. 13, pages 31-41, Wiley Intersciences, John Wiley & Sons, 1988 and by Vandorpe, et al in the Handbook of Biodegradable Polymers, edited by Domb, et al., Hardwood Academic Press, pp. 161-182 (1997). Polyanhydrides include those derived from diacids of the form HOOC-C.sub.6H.sub.4-O-(-CH.sub.2).sub.m-O-C.sub.6H.sub.4-COOH, where "m" is an integer in the range of from 2 to 8, and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150. Polyorthoesters such as those described by Heller in Handbook of Biodegradable Polymers, edited by Domb, et al., Hardwood Academic Press, pp. 99-118 (1997).

Figure 2:
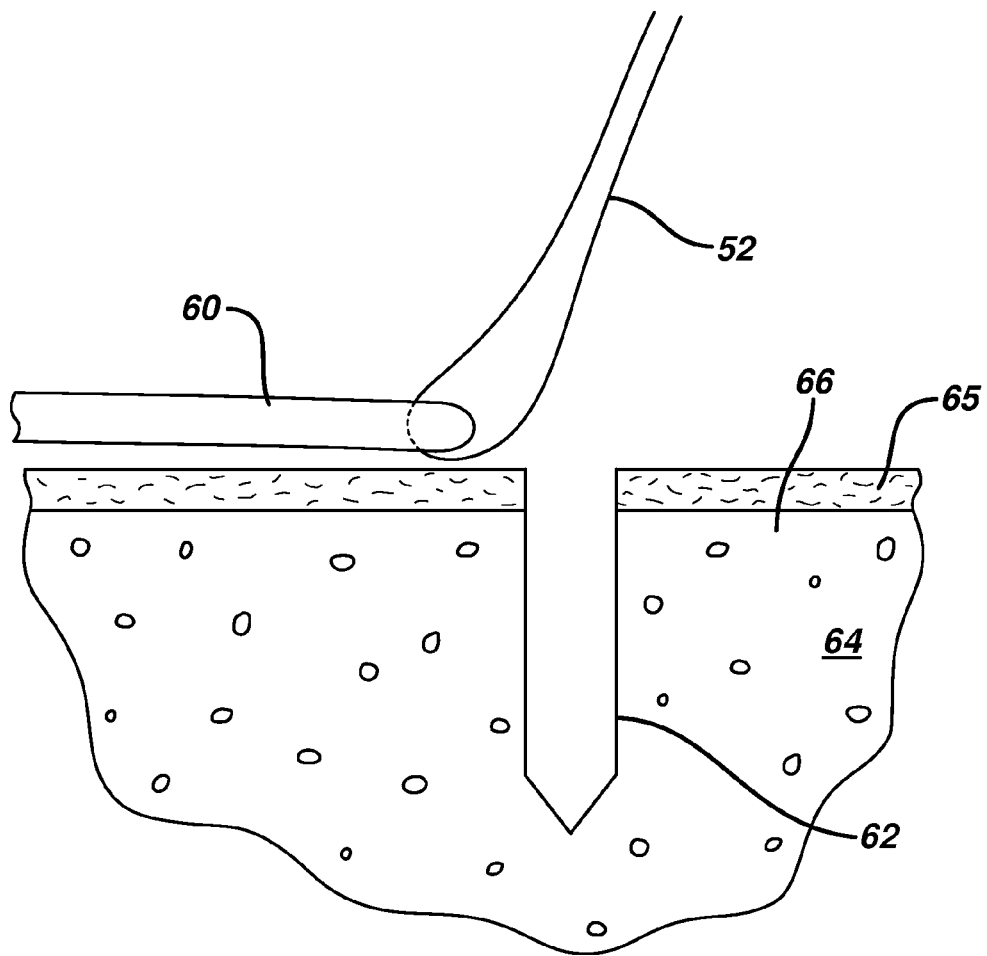
FIG. 2 is a side elevation view in cross-section of a bone and soft tissue.

Turning also now to FIG. 2, a length of the suture 52 has been threaded through a soft tissue 60 (such as for instance a rotator cuff tendon) adjacent a bone tunnel 62 prepared into a bone 64 (such as a humerus). The bone has a hard, outer cortical layer 65 and a softer inner cancellous portion 66.

Figure 3:
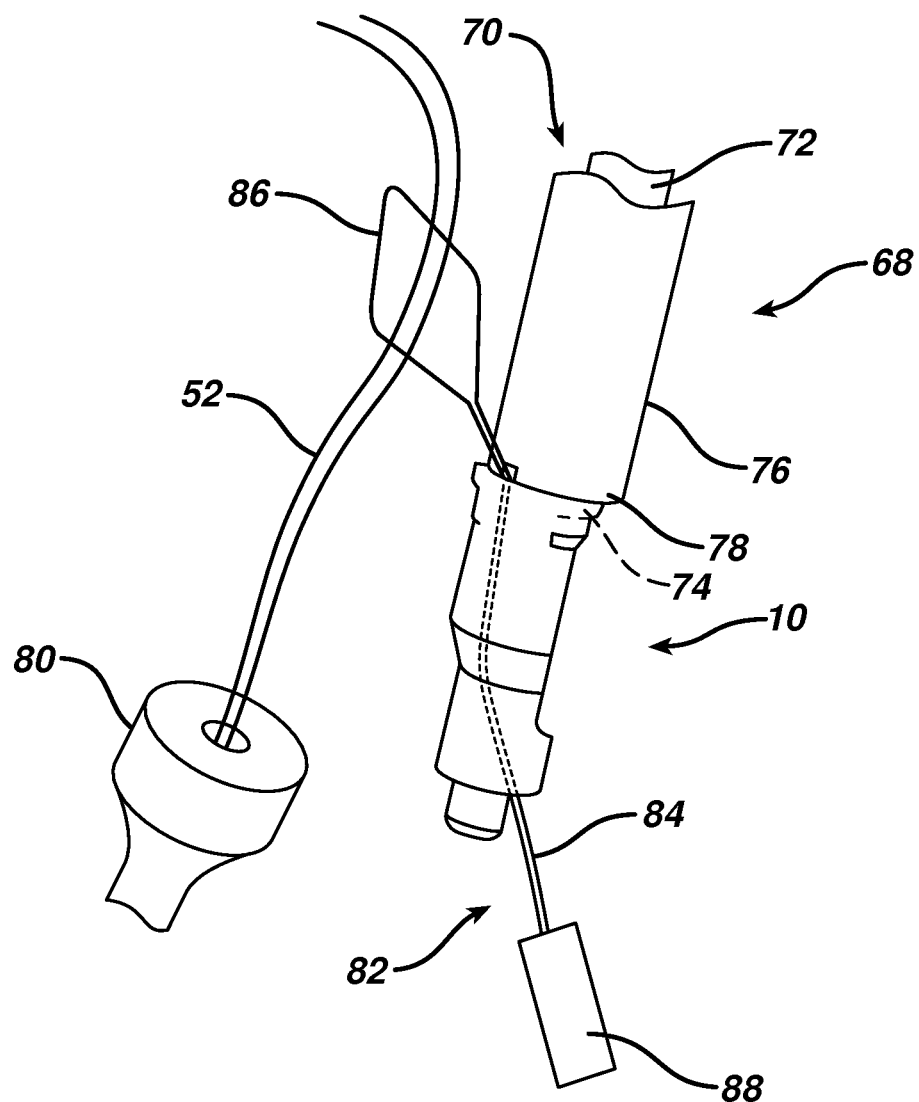
FIG. 3 is a perspective view of the suture anchor of FIG. 1 loaded onto a driver tool.

Turning also now to FIG. 3, the anchor 10 is loaded onto a driver tool 68. The driver 68 comprises an inner driver 70 comprising an elongated shaft 72 having a distal tool end 74 (such as a hex driver), which is co-axially received within an elongated outer tube 76. The tool end 74 is received within the tool receiving recess 38 of the anchor body 14 and a distal end 78 of the outer tube 76 abuts the shell proximal end 20.

The suture 52 from the soft tissue 60 extends up out of a cannula 80 used to access the bone tunnel 62 in an arthroscopic procedure. A suture threader 82 comprising an elongated flexible wire 84 having a distal suture capture loop 86 and a proximal threader tab 88 extends between the shell 12 and anchor member 14 along the suture path 54. The suture 52 is captured in the loop 86 and as the threader 82 is drawn along the path 54 the suture is drawn and threaded through the path 54 thus loading it into the anchor 10.

Figure 4:
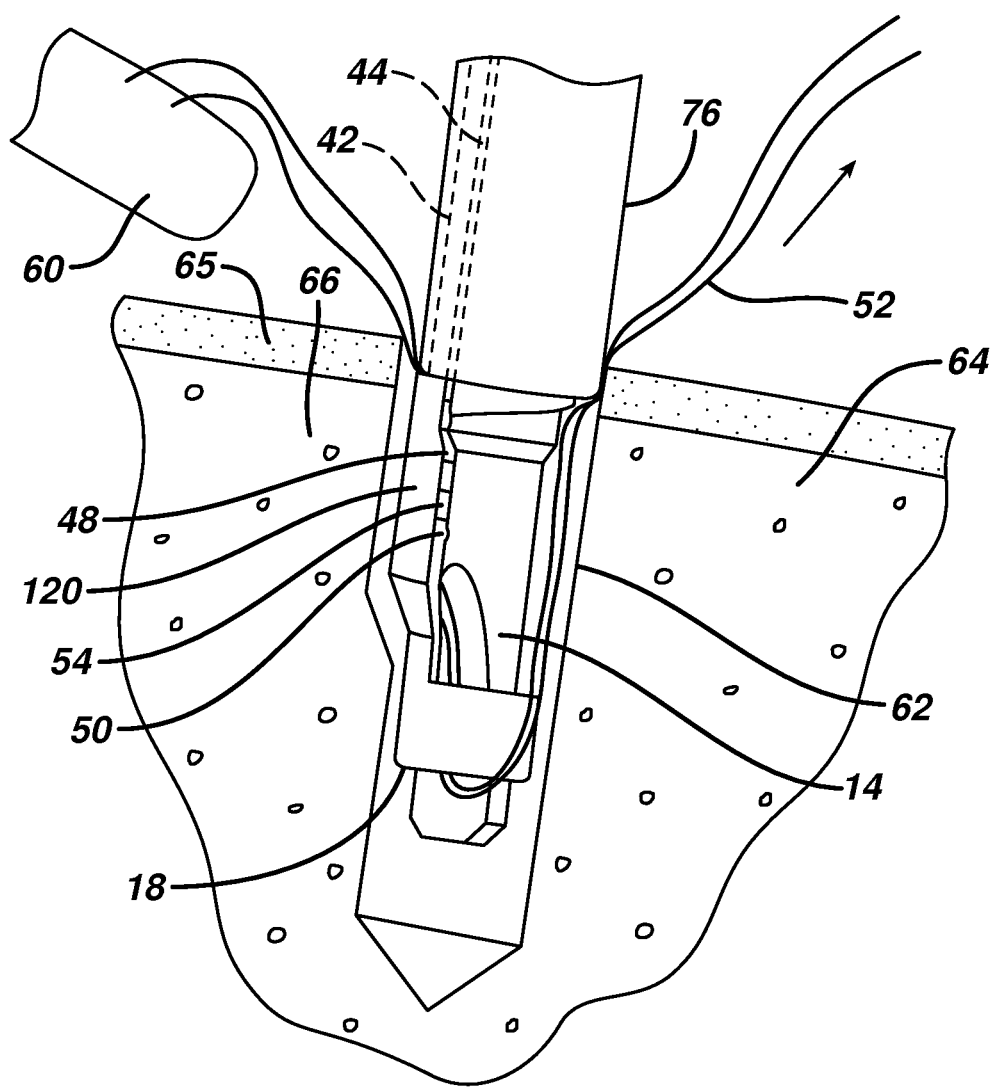
FIG. 4 is a side elevation view in cross-section bone of FIG. 2 into which the suture anchor of FIG. 1 is being initially implanted

Turning also now to FIG. 4, the suture anchor 10 on the driver tool 68, which carries the suture 52 from the soft tissue 60 and which has been fed down the cannula 80, is placed into the bone tunnel 62 with the cut-out 50 facing away from where the suture 52 passes through the soft tissue 60. Force on the outer tube 76 drives the shell 12 into the bone tunnel 62 beneath the surface of the bone 64. The anchor member threads 42 and 44 are not yet engaged with the shell threads 48 or the bone 64. The suture 52 extends from the soft tissue 60 to the anchor 10 and distally down the path 54 and then over the distal end 18 and back proximally up and out of the bone tunnel 62. The suture 52 is now tensioned to draw the soft tissue 60 into a desired position and to put a desired tension into the suture 52.

Figure 5:
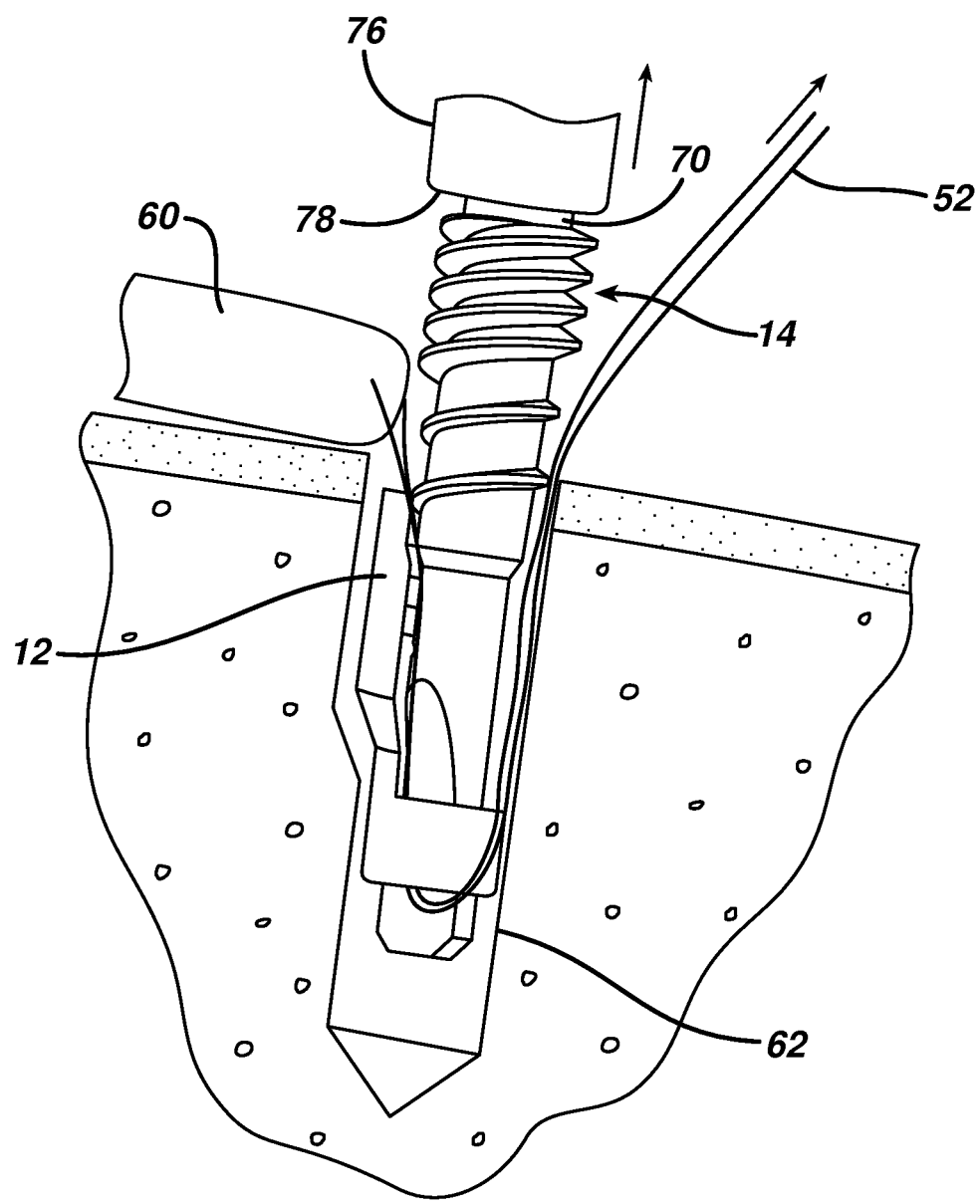
FIG. 5 is a side elevation view in cross-section showing an anchor member of the suture anchor of FIG. 1 being implanted.
Figure 6:
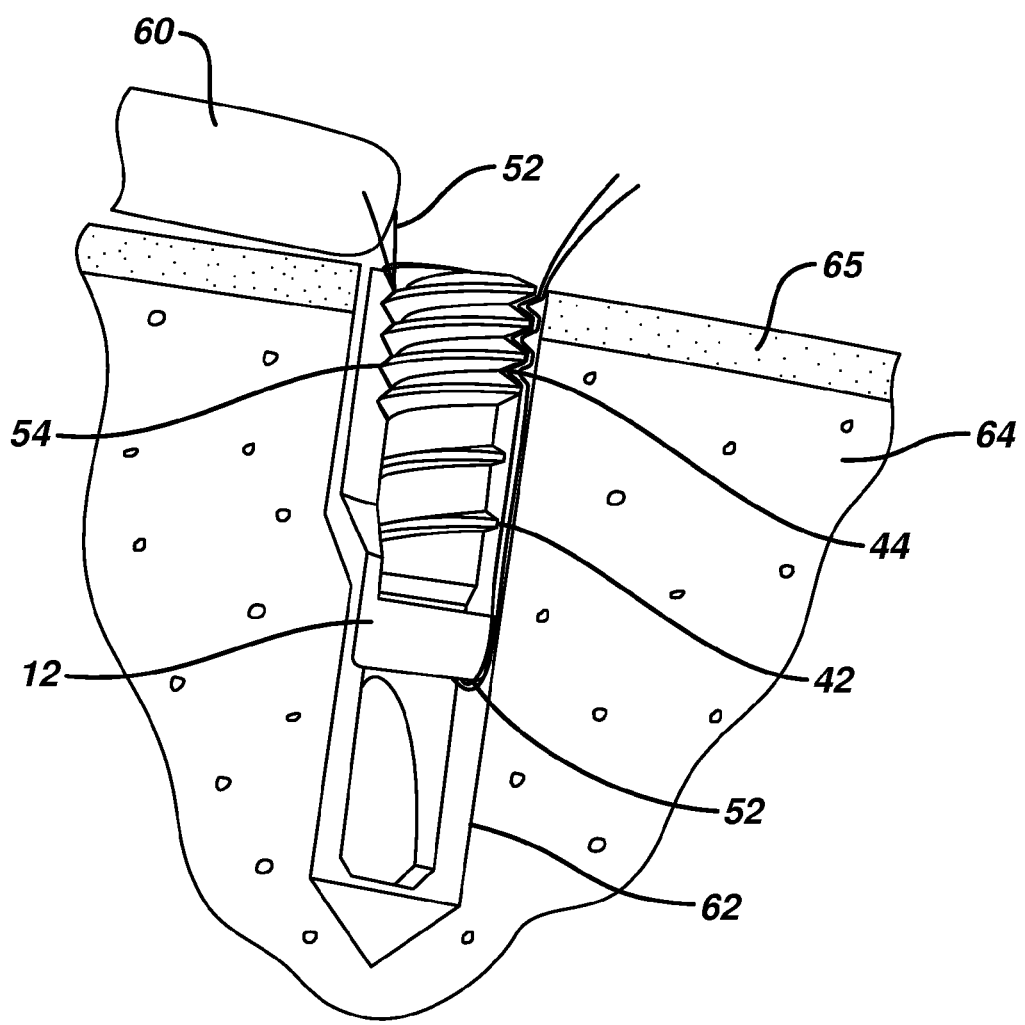
FIG. 6. is a side elevation view in cross-section showing the fully implanted suture anchor of FIG. 1.

Turning also now to FIG. 5, the outer tube 76 can be retracted and the inner driver 70 rotated to drive the anchor member 14 into the shell 12 and bone tunnel 62. With the anchor member 14 fully seated as shown in FIG. 6, the suture 52 is trapped between the shell 12 and the anchor member 14 along the path 54 and also between the bone 64 and the anchor member threads 42 and 44. The second thread 44 provides additional holding in the hard cortical bone 65. The shell 12 protects the suture 52 from cutting into the bone 64.

Figure 7A:
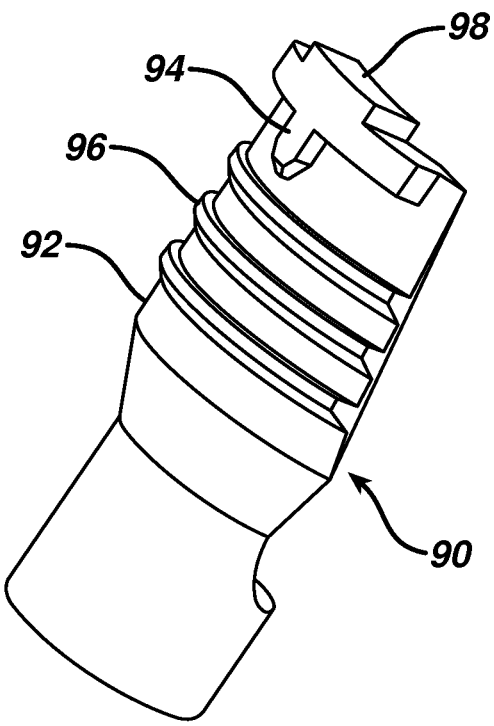
FIG. 7A is an outside perspective view of an alternative embodiment of a shell of a suture anchor according to the present invention.
Figure 7B:
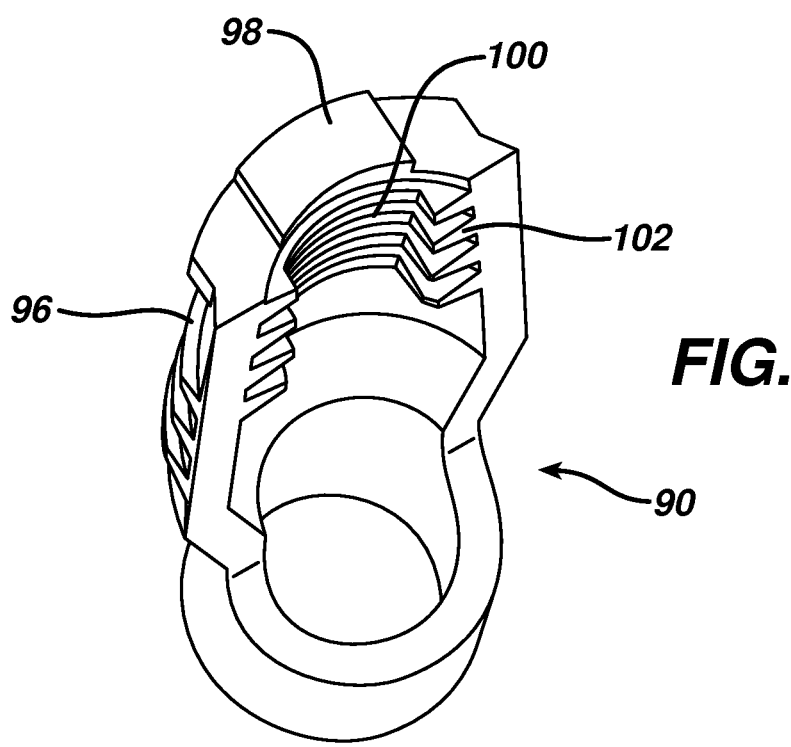
FIG. 7B is an inside perspective view of the shell of FIG. 7A.
Figure 8:
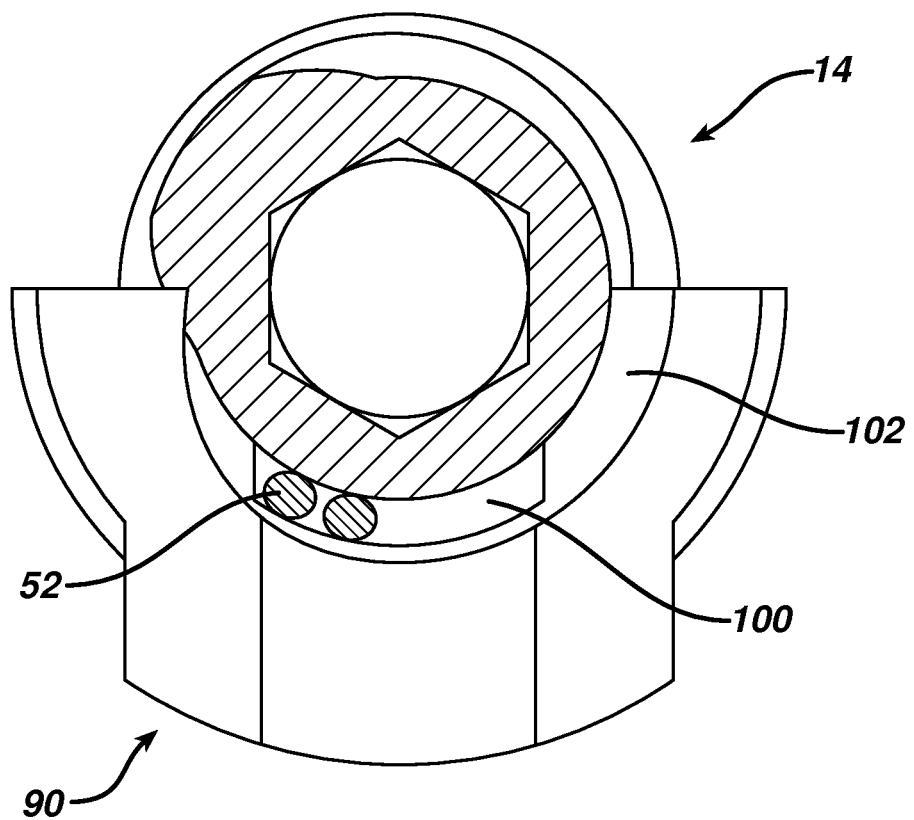
FIG. 8 is a top plan view of the shell of FIG. 7A with an anchor member (shown in section) disposed therein.

FIGS. 7A and 7B illustrate a further embodiment of a shell 90 similar to the shell 12 except that an exterior surface 92 of the sidewalls 22 has both longitudinal and lateral protruding fixation ridges 94 and 96 respectively. The lateral ridges 96 extend circumferentially about the shell 12 and provide additional holding force in a bone against pull-out. The longitudinal ridges 94 provide resistance against rotation induced by torque applied during implantation of the anchor member 12 (not shown in FIG. 7A or 7B). Alternatively, an anti-rotational engagement can be made between the shell 90 and the outer tube 76 to hold the shell against rotation as the anchor member is implanted. For instance one or more proximal protrusions 98 can be formed on the shell 90 and interface with mating indentations (not shown) on the outer tube distal end 76. This embodiment also shows a suture path 100 comprising a more distinct interruption in the internal threads 102.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. A suture anchor comprising a shell and an anchor member:
    the shell comprising a body having a distal end, a proximal end and sidewalls therebetween defining an axial cannulation therethrough;
    the anchor member comprising a body having a distal end and a proximal end, the anchor member body being sized to fit within the cannulation of the shell;
    the sidewalls defining a lateral cut-out such that with the anchor member received within the cannulation a first lateral portion of the anchor member protrudes laterally out of the shell and a second, laterally opposite, lateral portion of the anchor member is enclosed by the sidewalls;
    an exterior threading about the anchor member body, engaged with a complimentary internal threading on an interior surface of the sidewall;
    the exterior threading creating a friction enhancement on the first lateral portion frictionally engageable with a bone surface through the lateral cut-out when the suture anchor is disposed within a bone tunnel defined by the bone surface.

2. A suture anchor according to claim 1 wherein the cut-out extends to the shell proximal end.

3. A suture anchor according to claim 1 wherein the shell distal end completely encircles the anchor member.

4. A suture anchor according to claim 1 wherein a distal portion of the anchor member is smooth and free of the friction enhancement.

5. A suture anchor according to claim 1 and further comprising a suture locked between the sidewall and the anchor member.

6. A suture anchor according to claim 5 and further comprising an axially extending suture receiving recess along the sidewall adjacent the anchor member second lateral portion.

7. A suture anchor according to claim 5 wherein the suture extends proximally out of the shell over the proximal end of the shell.

8. A suture anchor according to claim 1 and further comprising a suture threaded distally down the cannulation between the sidewall and the anchor member, out of the cannulation at the shell distal end and up along the anchor member first lateral portion.

9. A suture anchor according to claim 1 and further comprising a suture threader extending between the anchor member and the sidewalls, the threader comprising an elongated flexible member, the flexible member extending out of the shell proximal end and terminating in a suture capture configuration.

10. A suture anchor according to claim 9 wherein the suture capture configuration comprises a suture capture loop.

\* \* \* \* \*